United States Patent [19]

Austin, Jr.

[11] 4,230,452

[45] Oct. 28, 1980

[54] MULTIPLE DENTAL HANDPIECE CONTROL SYSTEM

[76] Inventor: George K. Austin, Jr., P. O. Box 209, Rte. 2, Box 254, Newberg, Oreg. 97132

[21] Appl. No.: 36,053

[22] Filed: May 4, 1979

Related U.S. Application Data

[62] Division of Ser. No. 878,026, Feb. 15, 1978.

[51] Int. Cl.³ .............................................. A61C 1/02
[52] U.S. Cl. ..................................................... 433/28
[58] Field of Search ................. 433/27, 28; 91/189 R, 91/189 A; 137/596.14, 596.18, 637.1

[56] References Cited

U.S. PATENT DOCUMENTS

| | | | |
|---|---|---|---|
| Re. 28,649 | 12/1975 | Austin, Jr. | 433/78 |
| 3,672,059 | 6/1972 | Booth | 433/28 |
| 3,757,421 | 9/1973 | Kraft | 433/27 |

*Primary Examiner*—Robert Peshock
*Attorney, Agent, or Firm*—Klarquist, Sparkman, Campbell, Leigh, Hall & Whinston

[57] ABSTRACT

The specification discloses a multiple dental handpiece control system in which lifting one handpiece out of its hanger blocks supply of power and coolants to all other handpieces. Each handpiece has an individual control unit and a blockout unit. When a handpiece is lifted from its hanger, it actuates a valve to cause a piston in its control unit to shift to a condition causing supply of power and coolant fluid to that handpiece and cutting off power to the corresponding pistons in the other control units thereby preventing supply of power and coolant fluids to the other handpiece.

5 Claims, 3 Drawing Figures

MULTIPLE DENTAL HANDPIECE CONTROL SYSTEM

This is a division of application Ser. No. 878,026, filed Feb. 15, 1978.

DESCRIPTION

This invention relates to improved multiple dental handpiece control system and has for an object thereof the provision of a new and improved multiple dental handpiece control system.

Another object of the invention is to provide a multiple dental handpiece control system in which a first handpiece lifted out of its holder prevents operation of other handpieces until the first handpiece is returned to its holder.

A further object of the invention is to provide a multiple dental handpiece control system in which a plurality of handpieces are supplied with drive air and coolant fluids from individual modular control blocks, each block having a blocking diaphragm control valve which is closed by pressure from air through an associated control cylinder valve when the associated handpiece is in its hanger to actuate a hanger valve to keep the associated cylinder in one condition, the hanger valve serving, when the associated handpiece is lifted from its hanger, to change the associated cylinder to a second condition permitting operation of that handpiece and that cylinder also cutting off actuating air to the other cylinders when in its second condition.

IN THE DRAWINGS

Figure 1:
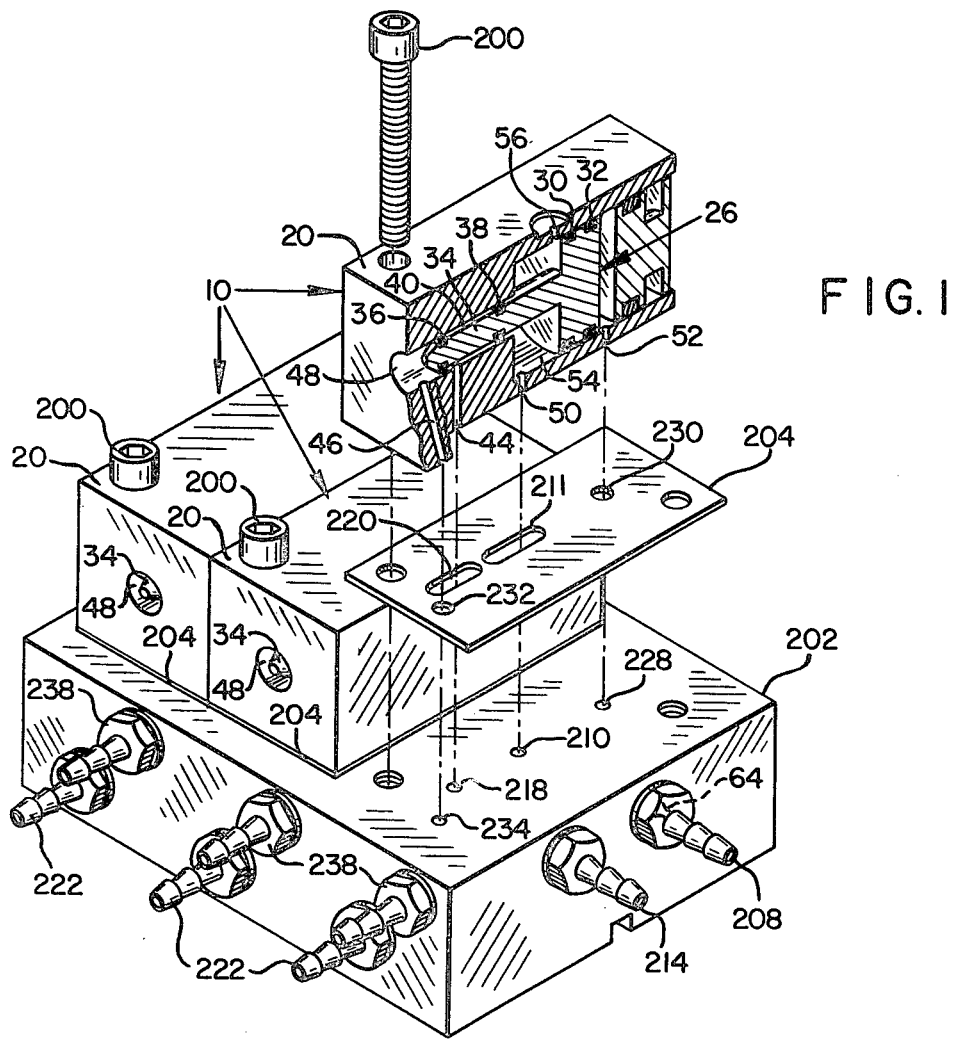
FIG. 1 is a partially exploded, perspective view of a portion of an improved multiple dental handpiece control system forming one embodiment of the invention.
Figure 3:
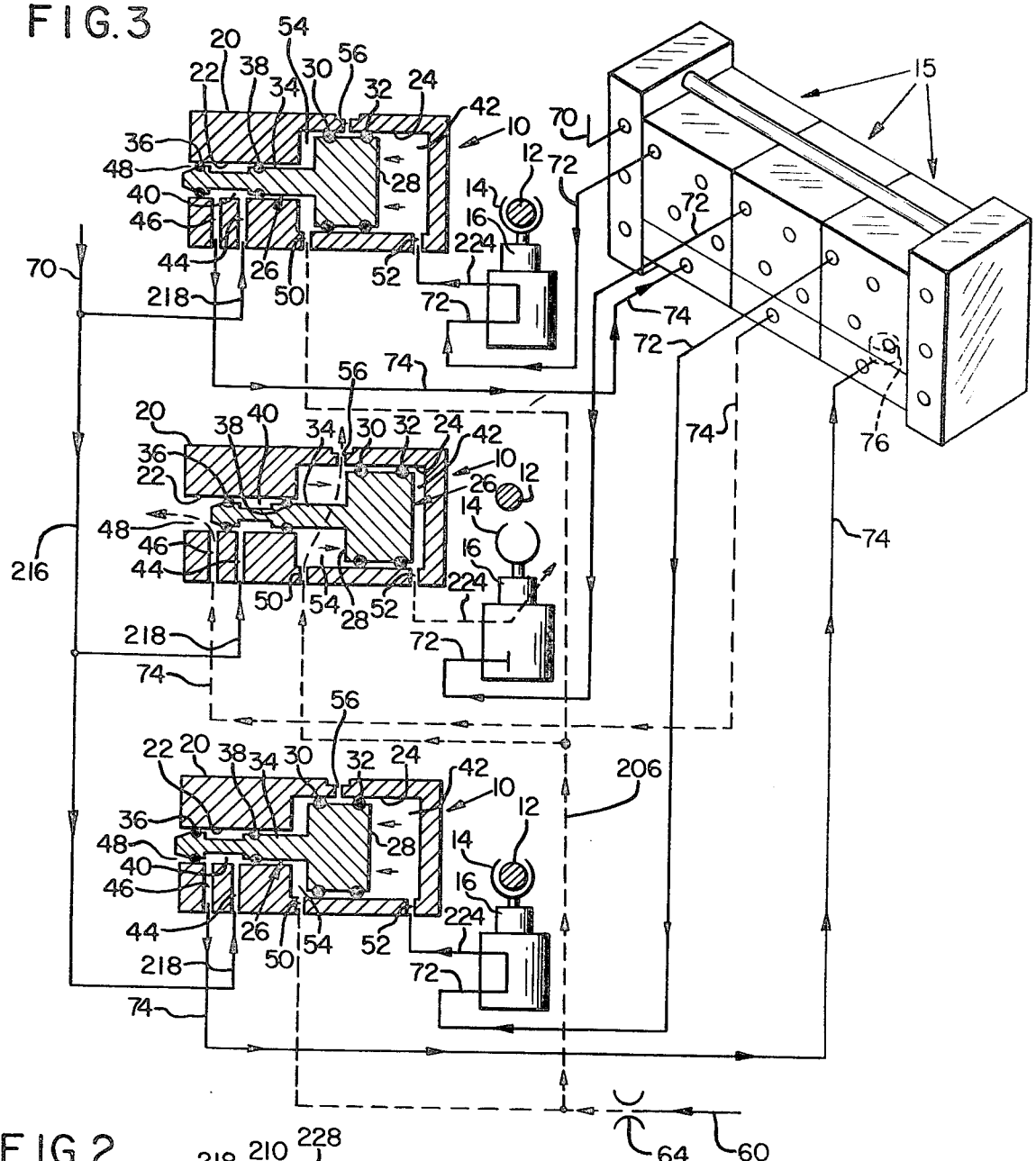
FIG. 3 is a partially sectional, partially perspective, schematic view of the system of FIG. 1.

An improved dental handpiece control system includes a plurality of valve units 10, one for each handpiece 12. The system includes holders or hangers 14 for holding the handpieces, each of which, when in its holder, actuates its hanger valve assembly 16 to prevent operation of that handpiece. The handpiece that is first taken from its holder 14 prevents operation of any handpiece subsequently removed from its holder until the first taken handpiece is returned to its holder. Each handpiece is supplied with drive air, coolant water and coolant air through one of a plurality of module control blocks 15 under the control of the hanger block assemblies 16. The construction and operation of the control blocks is identical to the construction and operation of the control blocks disclosed and claimed in my U.S. Pat. No. 3,638,310.

Each valve unit 10 includes a body 20 having a bore 22 and a counterbore 24. A piston 26 has a head 28 sealed by O-rings 30 and 32 and has a rod or stem 34 sealed in the bore 22 by O-rings 36 and 38. The piston, the bore and the O-rings form cavities or chambers 40, 54 and 42. The smaller diameter cavity 40 has leading thereto an inlet hole 44, an outlet hole 46 and a vent 48 (conveniently the open end of the bore). The larger diameter counterbore 24 (the control cavity) has two holes 50 and 52, one at either end, which serve as ports, alternately inlet and outlet, for the control air. The portion piston rod 34 has the seal rings 36 and 38 spaced such that the end ring 36 passes back and forth across the outlet hole 46 to connect the hole 46 either to vent 48 or inlet 44. The second seal ring 30 seals the small diameter cavity 40 from the large diameter cavity 54. The large diameter portion or head 28 carries the seal rings 30 and 32 which separate the counterbore 24 into the cavity 42 and cavity 54. Bleeder or vent hole or port 56 leads to the cavity 54 and a hole or port 52 leads into the cavity 42. As can be seen, introducing compressed air into chamber 54 through hole 50 will cause an unbalanced force on head 28 to move the piston to connect outlet hole 46 to vent 48. Relieving the air through hole 56 and pressurizing cavity 42 through hole 52 causes piston 26 to move to the left, as viewed in FIG. 1, to connect outlet 46 and inlet 44. Equal pressure (either zero psi or higher) on either side of piston head 28 does not tend to move the piston. However, there is a small force component toward the stem 34 due to the reduced piston area caused by the stem. This force component is much smaller than the friction force of the seal rings 30, 32, 36 and 38 so movement does not occur. A low pressure air supply line 60, of, for example, twenty pounds per square inch, may be used to control the valves 10 and perform the logic function necessary to allow the first handpiece out (lifted from its hanger) to operate and exclude all other handpieces from operation. In this system, holes 50 in all valve bodies are connected in parallel to a common supply source, a line 60 carrying low pressure air and a restrictor 64. The supply line 60 is equipped with a low volume restrictor 64 to allow the pressure at holes 50 to approach zero psi when any of the vent holes 56 are open. This also limits the venting air volume and slows the pressurizing time of holes 50 when the vents 56 are closed. When all vents 56 are closed, the pressure in cavity 54 slowly increases to the low pressure of line 60. A high pressure line 70 is connected by a passage through control blocks 15 to lines 72 connected to hanger block assemblies 16.

Figure 2:
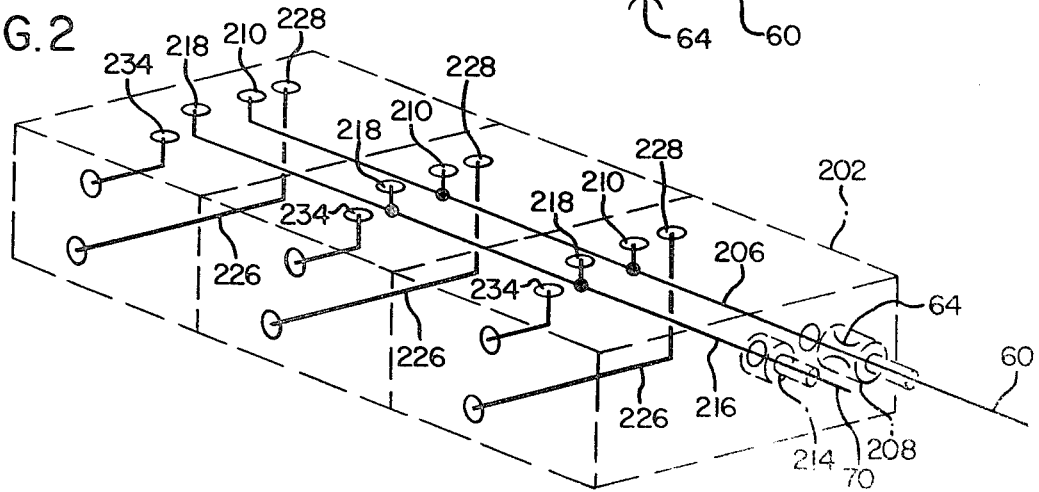
FIG. 2 is a schematic view of a portion of the system of FIG. 1.

As best shown in FIGS. 1 and 2, the valve units 10 may comprise a plurality of the cylinders 20 (with the pistons 26 therein) secured by screws 200 to a common manifold 202 with gaskets 204 therebetween. The manifold has a bore 206 supplied with the low pressure air from line 60 through a flow restrictor barb or connector 208. Ports 210 from the bore 206 lead to the ports 50 through holes 211 in the gasket 204. High pressure air is supplied from the line 70, which is connected to a barb or connector 214 leading to a bore 216 having ports 213 connected to the ports 44 through holes 220. Barbs 222 connected to lines 224 from the valves 16 are connected to bores 226 leading to ports 228 leading to the ports 52 through holes 230 in the gaskets 204. The ports 46 are connected to the lines 74 through holes 232 in the gaskets, ports 234 in the manifold, bores 236 in the manifold, and barbs or connectors 238.

OPERATION

With all handpieces 12 in their respective holders 14, cavities 42 through holes 52 are pressurized. This pressure causes all stems 34 to move until holes 44 and 46 are common and outlets 46 are pressurized. Pressurizing all of the outlets 46 causes all lines 74 to be pressurized to actuate valves 76 to block supplies of air and water to all the handpieces. In each the cavity 42 pressurizes through hole 52 to a pressure higher than in cavity 54 so that the pistons 26 do not move and thus are kept in their extreme lefthand positions. Removing one handpiece 12 from its holder relieves the pressure in cavity 42. This unbalances the forces on piston 26 such that the piston moves to the right to open port 46 to vent 48. Also, port 56 is opened and reduces the pressure in all cavities 54 to near zero psi. Only a small amount of air can bleed through restrictor 64, less than that permitted by the vents 56. Hence, when one of the other handpieces is removed from its hanger, it relieves the pressure in cavity 42, but since the pressure in each cavity 54 was previously reduced to near zero, the piston does not move, and pressure is maintained in the port 46 of the valve associated with the later removed handpiece. To reset the system and allow operation of a different handpiece, the "FIRST-OUT" handpiece must be replaced in its hanger. Replacing this handpiece in its holder activates its associated valve unit 10 pressurizing the cavity 42 causing piston 26 to connect inlet 44 and outlet 46, which pressurizes outlet 46, closing vent port 56 and pressurizing all the cavities 54.

What is claimed is:

1. In a multiple dental handpiece control system,
   a plurality of handpieces,
   a plurality of hanger mechanisms for holding the handpieces and each including valve means actuated when the handpiece associated therewith is removed from the associated hanger mechanism,
   a plurality of fluid supply control units for supplying fluids to the handpieces and each including disabling means,
   fluid supply means supplying fluid under pressure to the valve means,
   a plurality of cylinder mechanisms operable by the valve means and each including a piston and a cylinder,
   each valve means when actuated serving to actuate one of the cylinder mechanisms,
   a plurality of means operable by the cylinder mechanisms for actuating the disabling means,
   and preventing means operable by each cylinder mechanism when it is actuated for preventing actuation of the other cylinder mechanisms.

2. The control system of claim 1 wherein the preventing means includes a first port in each cylinder for supplying actuating fluid to the cylinder and an exhaust port in each cylinder opened when the cylinder is actuated.

3. In a multiple dental handpiece control system,
   a plurality of dental handpieces,
   a plurality of dental handpiece hanger mechanisms adapted to releasably hold the handpieces,
   a plurality of drive fluid supply means,
   a plurality of coolant fluid supply means,
   a plurality of master valve means operable when actuated to supply drive fluid and coolant fluid to the handpieces,
   a plurality of cylinders,
   a plurality of valve mechanisms operable by the cylinders for actuating the master valve means,
   and a plurality of hanger valve means actuated when a handpiece is removed from one of the hanger mechanisms to actuate one of the cylinders to actuate its valve means to actuate one of the master valve means,
   each cylinder serving while actuated to block actuation of the other cylinders.

4. In a multiple dental handpiece control system,
   a plurality of handpieces,
   a plurality of hanger mechanisms for holding the handpieces and each including valve means actuated when the handpiece associated therewith is removed from the associated hanger mechanism,
   a plurality of fluid supply control units for supplying fluids to the handpieces and each including disabling means,
   a plurality of cylinder mechanisms each including a piston and a cylinder,
   fluid supply means supplying fluid under pressure to the valve means,
   each valve means when actuated serving to actuate one of the cylinder mechanisms,
   a plurality of means operable by the cylinder mechanisms for actuating the disabling means, and means operable by each cylinder mechanism when it is actuated for preventing actuation of the other cylinder mechanisms.

5. In a multiple dental handpiece control system,
   a first handpiece,
   a second handpiece,
   a first hanger mechanism releasably holding the first handpiece,
   a second hanger mechanism releasably holding the second handpiece,
   a first cylinder having a first bore portion and a first counterbore portion,
   a second cylinder having a second bore portion and a second counterbore portion,
   a first piston having a first piston head and a first rod slidable in the first counterbore and bore portions of the first cylinder,
   a second piston having a second piston head and a second rod slidable in the second counterbore and the second bore portions of the second cylinder,
   first supply means for supplying fluids to the first handpiece including first disabling valve means operable when under pressure to prevent supply of fluids to the first handpiece,
   second supply means for supplying fluids to the second handpiece including second disabling valve means operable when under pressure to prevent supply of fluids to the second handpiece,
   first fluid under pressure supply means,
   second fluid under pressure supply means having restrictor means therein,
   each cylinder having a first port near one end of the counterbore, an exhaust port and a supply port near the other end thereof,
   hanger valve means connecting the first fluid under pressure supply means to the first port of each cylinder,
   common means connecting the second fluid under pressure supply means to the supply port of both cylinders,
   each piston head serving to close the exhaust port when the piston is in a first position and open the exhaust port to the supply port when the piston is in a second position,
   each cylinder having a second supply port and a further port spaced along the bore portion,
   each piston rod serving to connect the second supply port and the further port when the piston is in its first position and to close the second supply port and open the further port to exhaust when that piston is in its second position,
   and a plurality of means connecting each further port individually to the disabling valve means.

* * * * *